United States Patent [19]

Payne et al.

[11] Patent Number: 4,931,196
[45] Date of Patent: Jun. 5, 1990

[54] LUBRICANT COMPOSITION CONTAINING MULTIFUNCTIONAL LUBRICANT ADDITIVES

[75] Inventors: John D. Payne; Robert M. O'Neil, both of Manchester, England

[73] Assignee: Ciba-Geigy Corporation, Ardsley, N.Y.

[21] Appl. No.: 275,816

[22] Filed: Nov. 25, 1988

[30] Foreign Application Priority Data

Dec. 8, 1987 [GB] United Kingdom ............... 8728675

[51] Int. Cl.$^5$ .................................... C10M 135/00
[52] U.S. Cl. .............................. 252/47.5; 252/394; 544/219
[58] Field of Search ............... 252/47.5, 394; 544/219

[56] References Cited

U.S. PATENT DOCUMENTS

| | | | |
|---|---|---|---|
| 2,676,151 | 4/1954 | Loughran et al. | 544/219 |
| 2,836,564 | 5/1958 | Roberts et al. | 252/47.5 |
| 3,156,690 | 11/1964 | Dexter et al. | 252/47.5 |
| 4,038,197 | 7/1977 | Caspari | 252/47.5 |

FOREIGN PATENT DOCUMENTS

| | | |
|---|---|---|
| 063327 | 10/1982 | European Pat. Off. |
| 0223916 | 6/1987 | European Pat. Off. |
| 233916 | 6/1987 | European Pat. Off. |
| 1328169 | of 1963 | France |

OTHER PUBLICATIONS

Chemical Abstract, vol. 96 (1982), 96:165184h.
Chemical Abstract, vol. 85 (1976), 85:21482d.
Chemical Abstracts, 90:249w.

Primary Examiner—William R. Dixon, Jr.
Assistant Examiner—Jerry D. Johnson
Attorney, Agent, or Firm—Stephen V. O'Brien

[57] ABSTRACT

The present invention provides a lubricant composition comprising a lubricating oil and, as a multifunctional additive, at least one compound of formula (I)

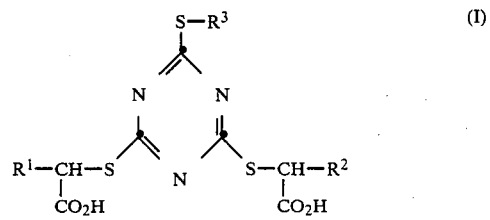

in which $R^1$ and $R^2$ are, independently, hydrogen or $C_1$-$C_{20}$ alkyl and $R^3$ is hydrogen, $C_1$-$C_{20}$ alkyl or a group of the formula

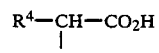

wherein $R^4$ is H or $C_1$-$C_{20}$ alkyl. Most of the compounds of formula I are new.

8 Claims, No Drawings

LUBRICANT COMPOSITION CONTAINING MULTIFUNCTIONAL LUBRICANT ADDITIVES

This invention relates to new lubricant compositions containing multifunctional lubricant additives; to their use as multifunctional lubricant additives; to new compounds and to their production by reaction of 2,4,6-trimercapto-1,3,5-triazine (trithiocyanuric acid) with alpha-halogenated aliphatic carboxylic acids.

The effective protection of metallic equipment from corrosion is a long standing problem. This problem is particularly acute in an environment in which ferrous metal comes into contact with a lubricant which may be contaminated with water, as in steam turbine oils.

Another problem is presented by the friction generated between rubbing metal surfaces. This results in wear and occurs, for example, on the metallic parts in an apparatus such as a hydraulic pump. In addition, under conditions of high load, breakdown of the lubricant and seizure of metallic parts may occur.

As an attempted solution to these problems, it is known that many lubricant additives will impart protection against one of corrosion, wear, extreme pressure or oxidation. However, additives which provide simultaneous protection against more than one of these phenomena are less common.

In U.S. Pat. No. 2,836,564 there are disclosed new reaction products of alpha-halogenated aliphatic monocarboxylic acids and 2,5-dimercapto-1,3,4-thiadiazole and their use as rust inhibitors. In European Pat. No. 223,916 there are disclosed new reaction products of alpha-halogenated half esters or amides of succinic acid and thiazole dimercaptides and their use as multifunctional lubricant additives.

The present invention provides a lubricant composition comprising a lubricating oil and, as a multifunctional additive, at least one compound of formula (I)

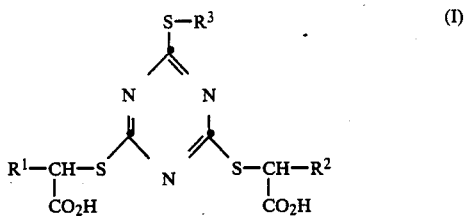

in which $R^1$ and $R^2$ are, independently, hydrogen or $C_1$-$C_{20}$ alkyl and $R^3$ is hydrogen, $C_1$-$C_{20}$ alkyl or a group of formula

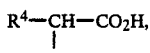

wherein $R^4$ is H or $C_1$-$C_{20}$ alkyl.

We have found certain new compounds, obtainable by reaction of 2,4,6-trimercapto-1,3,5-triazine with alpha-halogenated aliphatic carboxylic acids which impart simultaneous superior rust inhibiting, anti-wear, extreme pressure and antioxidant properties when incorporated into a lubricant.

The new compounds of the present invention have the formula (I):

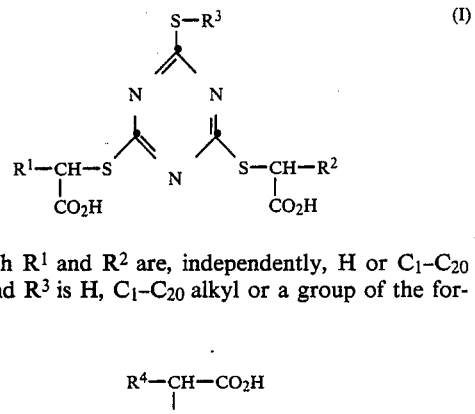

in which $R^1$ and $R^2$ are, independently, H or $C_1$-$C_{20}$ alkyl and $R^3$ is H, $C_1$-$C_{20}$ alkyl or a group of the formula

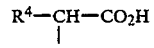

wherein $R^4$ is H or $C_1$-$C_{20}$ alkyl with the proviso that when $R^3$ is $-CH_2CO_2H$ then $R^1$ and $R^2$ may not simultaneously be hydrogen.

When $R^1$, $R^2$, $R^3$ and $R^4$ are alkyl, the alkyl group may be straight or branched.

Examples of $C_1$-$C_{20}$ alkyl groups $R^1$, $R^2$, $R^3$ and $R^4$ include methyl, ethyl, propyl, isopropyl, butyl, isobutyl, octyl, isooctyl, nonyl, decyl, undecyl, dodecyl, isododecyl, tridecyl, tetradecyl, pentadecyl, hexadecyl, isohexadecyl, heptadecyl, octadecyl, isooctadecyl, eicosyl, isoeicosyl and isoamyl, 2-ethylbutyl, 1-methylpentyl, 1,3-dimethylbutyl, 1,1,3,3-tetramethylbutyl, 2-ethylhexyl, 1-methylhexyl, 1-methylheptyl, 1,1,3-trimethylhexyl and trimethylundecyl.

Preferred compounds of formula (I) are those in which $R^1$ and $R^2$ are $C_8$-$C_{20}$ alkyl and $R^3$ is $C_8$-$C_{20}$ alkyl or $R^4$-CH-$CO_2H$ in which $R^4$ is $C_1$-$C_{20}$ alkyl.

Specific examples of compounds of formula I are indicated in the following Table.

| $R^1$ | $R^2$ | $R_3$ |
|---|---|---|
| H | H | H |
| H | $CH_3$ | $CH_3$ |
| H | H | $CH_3$ |
| $CH_3$ | $CH_3$ | $CH_3$ |
| $C_2H_5$ | $CH_3$ | H |
| $C_2H_5$ | $C_2H_5$ | H |
| $C_2H_5$ | $C_2H_5$ | $C_2H_5$ |
| $C_{10}H_{21}$ | $C_{10}H_{21}$ | $C_{10}H_{21}$ |
| $C_{20}H_{41}$ | $C_{20}H_{41}$ | $C_{20}H_{41}$ |
| H | $CH_3$ | $-CH_2CO_2H$ |
| $CH_3$ | $CH_3$ | $-CH_2CO_2H$ |
| H | H | $-CH(CH_3)CO_2H$ |
| H | $CH_3$ | $-CH(CH_3)CO_2H$ |
| H | H | $-CH(C_{18}H_{37})CO_2H$ |

The present invention also provides a process for the production of new compounds of the invention by reacting trithiocyanuric acid under alkaline conditions with 3 molar equivalents of an alpha-halogenated aliphatic carboxylic acid capable of introducing the groups

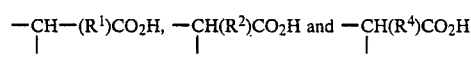

in which $R^1$, $R^2$ are, independently, hydrogen or $C_1$-$C_{20}$ alkyl and $R^4$ is hydrogen or $C_1$-$C_{20}$ alkyl; or with 2 molar equivalents of an alpha-halogenated aliphatic carboxylic acid capable of introducing the groups $$-\underset{|}{CH}(R^1)CO_2H \text{ and } -\underset{|}{CH}(R^2)CO_2H$$

and one molar equivalent of an alkyl halide of formula $R^3$-halide in which R3 is hydrogen, $C_1$–$C_{20}$ alkyl or a group of formula $$R^4-\underset{|}{CH}-CO_2H,$$

wherein $R^4$ is hydrogen or $C_1C_{20}$ alkyl.

The reaction of 2,4,6-trimercapto-1,3,5-triazine under alkaline conditions with either 3 molar equivalents of an alpha-halogenated aliphatic carboxylic acid or 2 molar equivalents of an alpha-halogenated aliphatic carboxylic acid and one molar equivalent of an alkyl halide is illustrated e.g. by reaction schemes (1) and (2):

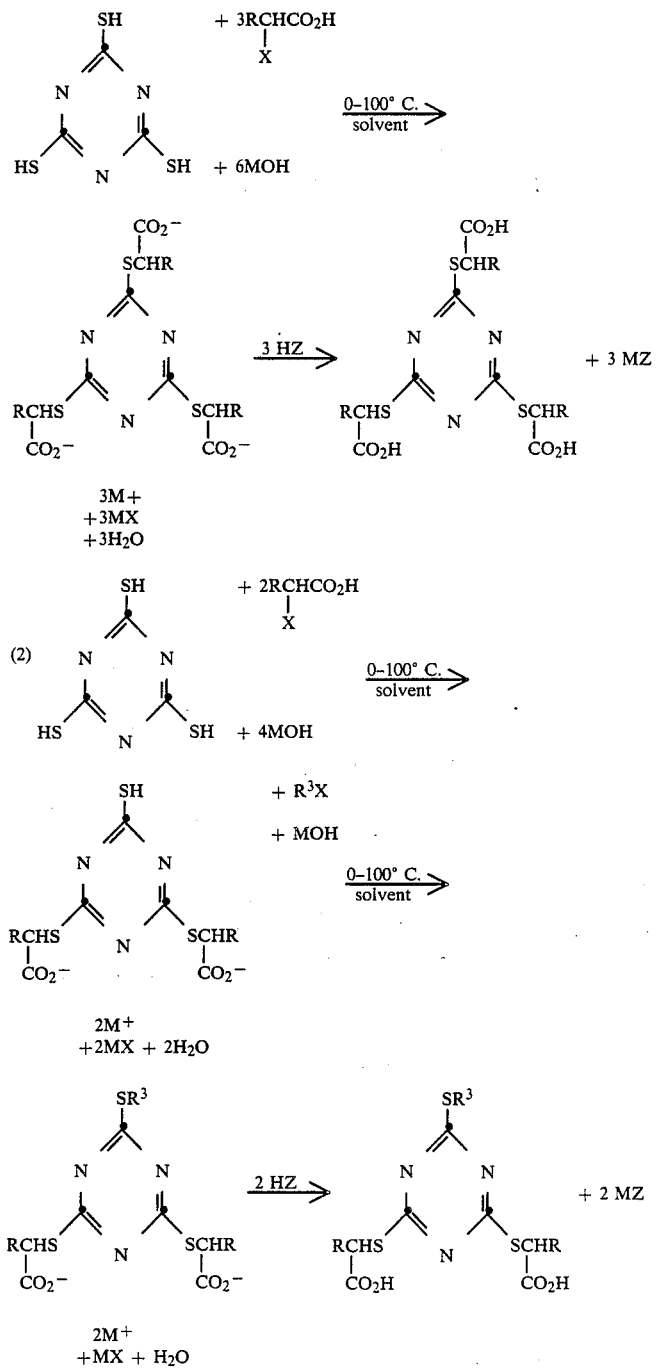

where
R=$R^1$ or $R^2$

M=NH₄, Li, Na or K;
X=Cl or Br; and
HZ represents an inorganic acid e.g. HCl.

The reaction scheme (1) may be carried out by treating, at below ambient temperature, 2,4,6-trimercapto-1,3,5-triazine with 6 molar equivalents of an alkali metal hydroxide dissolved in alcohol and subsequent addition of 3 molar equivalents of an alpha-halogenated aliphatic carboxylic acid to the reaction mixture. The reaction mixture may then be allowed to warm to ambient temperature and may be then heated under reflux for a period of several hours. Ethyl alcohol is most suitable as reaction solvent but other solvents such as methanol, isopropanol and butanol may be used. Upon cooling, the reaction solvent may be removed, the residue acidified and the product isolated by solvent extraction.

The reaction scheme (2) may be carried out in a similar manner with the exception that the 2,4,6-trimercapto-1,3,5-triazine may be treated initially with 4 molar equivalents of alkali and 2 molar equivalents of an alpha-halogenated aliphatic carboxylic acid. After a period of heating under reflux, the reaction mixture may be cooled and treated with a further molar equivalent of alkali and alkyl halide and then heated to reflux. The product may be isolated in the same manner as described in the scheme according to scheme (1).

The compounds of formula (I) are active in imparting desirable properties to lubricants. They are particularly effective as corrosion inhibitors, antiwear and extreme pressure agents and also have some antioxidant properties. The said compounds are effective in amounts of e.g., 0.01–5 wt %, especially 0.02–1 wt % based on the lubricant.

Preferred are lubricant compositions wherein the lubricating oil is a turbine oil or a hydraulic oil.

The lubricating oil may be a mineral oil, a synthetic oil or any mixture of such oils. Mineral oils are preferred and examples of these include paraffinic hydrocarbon oils e.g. a mineral oil having a viscosity of 46 mm²/s at 40° C.; "150 Solvent Neutral" a solvent refined neutral mineral oil having a viscosity of 32 mm²/s at 40° C.; and "Solvent brightstocks", a high boiling residue from the process of refining mineral oil, and having a viscosity of 46 mm²/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula:

R⁵—OOC—alkylene—COOR⁶ wherein "alkylene" denotes an alkylene residue having from 2 to 14 carbon atoms and R⁵ and R⁶ are the same or different and each is an alkyl group having from 6 to 18 carbon atoms. Tri-esters which are of use as lubricating oil base stocks are those derived from trimethylolpropane and C₆–C₁₈ mono-carboxylic acids or mixtures thereof, whereas suitable tetraesters include those derived from pentaerythritol and a C₆–C₁₈ monocarboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from an aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoffe und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

EXAMPLES OF PHENOLIC ANTIOXIDANTS

1. Alkylated Monophenols 2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclcopentyl-4-methylphenol, 2-(β-methylcyclohexyl)-4,6-dimethylphenol, 2,6-di-octadecyl-4-methylphenol, 2,4,6-tricyclohexylphenol, 2,6-di-tert-butyl-4methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octadecyloxyphenol.

3. Hydroxylated Thiodiphenylethers 2,2'-Thio-bis-(6-tert-butyl-4-methylphenol), 2,2'-thio-bis-(4-octylphenol), 4,4'-thio-bis-(6-tert-butyl-3-methylphenol), 4,4'-thio-bis(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-dimethylbenzyl)-4-nonylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)-butane, 2,6-di-(3-tert-butyl-5-methyl-2-hydroxybenzyl)-4-methylphenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis-(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethylbenzyl)dithiolterephthalate, 1,3,5-tris-(3,5-di-tertbutyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4- hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenol)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, bis-hydroxyethyl-oxalic acid diamide.

8. Esters of β-(5-tert-butyl-4-hydroxy-3-methyl-phenyl)-propionic acid with mono- or polyhydric alcohols, for example with methanol, diethyleneglycol, octadecanol, triethyleneglycol, 1,6-hexanediol, pentaerythritol, neopentylglycol, tris-hydroxyethyl-isocyanurate, thiodiethyleneglycol, di-hydroxyethyl-oxalic acid diamide.

9. Amides of β-(3,5-Di-tert-butyl-4-hydroxyphenyl)-propionic acid for example
N,N'-Bis-(3,5-di-tert-butyl-4-hydroxyphenylpropionyl)-hexamethylene-diamine, N,N'-bis-(3,5-di-tert-butyl-4-hydroxyphenylpropionyl)-trimethylene-diamine, N,N'-bis-(3,5-di-tert-butyl-4-hydroxyphenylpropionyl)-hydrazine.

Examples of amine antioxidants:
N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylamino-phenol, 4-dodecanoylamino-phenol, 4-octadecanoylamino-phenol, di-(4-methoxy-phenyl)-amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-(1',3'-dimethyl-butyl)phenyl]amine, tert-octylated N-phenyl-1-naphthylamine, mixture of mono-and dialkylated tert-butyl-/tert-octyldiphenylamines, 2,3-dihydro-3,3-dimethyl-4H-1,4-benzothiazine, phenothiazine, n-allyl-phenothiazine.

Examples for other antioxidants:
Aliphatic or aromatic phosphites, esters of thiodipropionic acid or of thiodiacetic acid, or salts of dithiocarbamic or dithiophosphoric acid.

Examples of metal passivators, for example for copper, are:
Triazoles, benzotriazoles and derivatives thereof, tolutriazole and derivatives thereof, 2-mercaptobenzothiazole, 2-mercaptobenzotriazole, 2,5-dimercapto-thiadiazole, 2,5-dimercaptobenzotriazole, 5,5'-methylene-bis-benzotriazole, 4,5,6,7-tetrahydrobenzotriazole, salicylidene-propylenediamine and salicylaminoguanidine and salts thereof, 1,2,4-triazole and N,N-disubstituted aminomethyl triazoles of formula

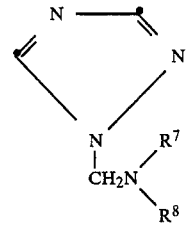

in which $R^7$ and $R^8$ are, independently, e.g. alkyl, alkenyl, or hydroxyethyl, obtained by reacting 1,2,4-triazole with formaldehyde and an amine $HNR^7R^8$, as disclosed in European Patent Application No. 160620; and the Mannich reaction products derived from benzotriazole or tolutriazole, formaldehyde and an amine $HNR^7R^8$.

Examples of rust inhibitors are:

(a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amides, 4-nonyl-phenoxy-acetic acid.

(b) Nitrogen-containing compounds, e.g.

I. Primary, secondary or tertiary aliphatic or cycloaliphatic amines and amine-salts of organic and inorganic acids, e.g. oil-soluble alkylammonium carboxylates.

II. Heterocyclic compounds, e.g. substituted imidazolines and oxazolines.

(c) Phosphorus-containing compounds, e.g.
amine salts of phosphonic acid or phosphoric acid partial esters, zinc dialkyldithio phosphates.

(d) Sulfur-containing compounds, e.g.
barium-dinonylnaphthalene-n-sulfonates, calcium petroleum sulfonates.

(e) Derivatives of gamma- alkoxypropylamines described in Japanese Patent Publication No. 15783/1973; and (f) Salts having the formula $Y—NH_3—R^9CO_2^-$ in which Y is a group $R^{10}X_1CH_2CH(OH)CH_2$ in which $R^9$ and $R^{10}$, independently, are e.g. alkyl and $X_1$ is O,-$CO_2$, NH, N(alkyl), N(alkenyl) or S, these salts being prepared by mixing an amine $Y—NH_2$ with an acid $R^9CO_2H$, as disclosed in DE-OS 34 37 876 (German Offenlegungsschrift).

(g) Compounds having the formula

$R^a—X_2—CH_2—CH(OH)—CH_2NR^bR^c$ in which $X_2$ is —O—, —S—, —$SO_2$,—C(O)—O— or —N($R^d$) in which $R^d$ is H or $C_1-C_{12}$ alkyl, $R^b$ is unsubstituted $C_1-C_4$ alkyl or $C_2-C_5$ alkyl substituted by one to three hydroxyl groups, $R^c$ is hydrogen, unsubstituted $C_1-C_4$ alkyl or $C_2-C_5$ alkyl substituted by one to three hydroxyl groups provided that at least one of $R^b$ and $R^c$ is hydroxy-substituted, and $R^a$ is $C_2-C_{20}$ alkyl —CH$_2$—CH(OH)—CH$_2NR^bR^c$ or $R^a$ is $C_2-C_{18}$ alkenyl, $C_2-C_3$ alkynyl or $C_5-C_{12}$ cycloalkyl provided that, when $X_2$ is —O— or —C(O)—O—, $R^a$ is branched $C_4-C_{20}$ alkyl. These compounds are described in GB Patent Specification 2172284A.

(h) Compounds having the formula:

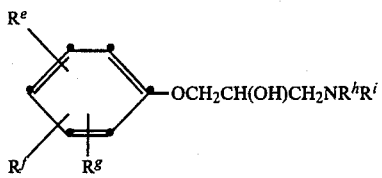

in which $R^e$, $R^f$, $R^g$ are, independently, hydrogen, $C_1$-$C_{15}$ alkyl, $C_5$-$C_{12}$cycloalkyl, $C_6$-$C_{15}$ aryl or $C_7$-$C_{12}$ aralkyl and $R^h$ and $R^i$, independently, are hydrogen, 2-hydroxyethyl or 2-hydroxypropyl, provided that $R^h$ and $R^i$ are not simultaneously hydrogen and, when $R^h$ and $R^i$ are each —$CH_2CH_2OH$, $R^e$ and $R^f$ are not simultaneously hydrogen and $R^g$ is not pentyl. These compounds are described in EP Patent Specification 0 252 007.

Examples of viscosity-index improvers are:

Polyacrylates, polymethacrylates, vinylpyrrolidone/methacrylate-copolymers, polyvinylpyrrolidones, polybutenes, olefin-copolymers, styrene/acrylate-copolymers, polyethers.

Examples of pour-point depressants are:

Polymethacrylates, alkylated naphthalene derivatives.

Examples of dispersants/detergents are:

Polybutenylsuccinic acid-amides or -imides, polybutenylphosphonic acid derivatives, basic magnesium-, calcium-, and bariumsulfonates and -phenolates.

Examples of anti-wear additives and extreme pressure additives are:

Sulfur- and/or phosphorus- and/or halogen-containing compounds e.g. sulfurised vegetable oils, zinc dialkyldithiophosphates, tritolylphosphate, chlorinated paraffins, alkyl- and aryldi- and trisulfides, triphenylphosphorothionate, diethanolaminomethyltolutriazole, di(2-ethylhexyl)-aminomethyltolutriazole.

The present invention also includes a process of improving the rust inhibiting, antiwear, extreme pressure and antioxidant properties of lubricating oils by incorporation of at least one compound of formula I, as mentioned above, into said lubricant.

Further, the present invention includes the use of at least one compound of formula I, as mentioned above, in a lubricating oil in order to improve the rust inhibiting, antiwear, extreme pressure and antioxidant properties thereof.

The following examples further illustrate the invention:

In these examples, all parts and percentages given are by weight unless otherwise specified.

Example 1 Preparation of 2,2′, 2″-[1,3,5-triazine-2,4,6-triyltris-(thio)]tris dodecanoic acid A stirred solution of KOH (12.8 g; 0.228 mole) in ethanol (350 ml) is cooled to 10° C. and treated with trithiocyanuric acid (6.8 g; 0.038 mole). After stirring for 30 minutes, the reaction mixture is treated with 2-bromododecanoic acid (31.8 g; 0.114 mole) in small portions over 10–15 minutes. The resulting thick, white suspension is stirred for a further 30 minutes at 10° C. and is then allowed to warm to ambient temperature. Upon reaching ambient temperature the reaction mixture is heated to reflux and maintained at this temperature for 6 hours.

The reaction mixture is cooled to ambient temperature and the solvent is removed under reduced pressure. The white, waxy residue is suspended in water (150 ml) and acidified with concentrated HCl to pH 1. The acidified aqueous suspension is then extracted with ether (200 ml) and the ether extract is washed with water (2×80 ml). The extract is dried over $MgSO_4$, filtered, then evaporated to yield 25.9 g (88 %) of a yellow waxy solid product.

Analysis Found: C 60.65 %; H 9.19 %; N 5.67 %.

$C_{39}H_{69}N_3O_6S_3$ requires: C 60.66 %; H 9.01 %; N 5.44 %.

Example 2 Preparation of 2,2′, 2″-[1,3,5-triazine-2,4,6-triyltris-(thio)]tris octadecanoic acid.

The procedure of Example 1 is repeated but substituting 2-bromooctadecanoic acid for 2-bromododecanoic acid. The product is a yellow solid, mp 37° C., obained in 68 % yield.

Analysis Found: C 65.76 %; H 10.39 %; N 3.97 %.

$C_{57}H_{105}N_3O_6S_3$ requires: C 66.81 %; H 10.33 %; N 4.10 %.

Example 3 Preparation of 2,2′-[2-dodecylthio-1,3,5-triazine-4,6-diylbis-(thio)]bis dodecanoic acid.

A stirred solution of KOH (5.6 g; 0.1 mole) in ethanol (100 ml) is cooled to 5–10° C. and treated with trithiocyanuric acid (4.42 g; 0.025 mole). After stirring for 30 minutes, the reaction mixture is treated with 2-bromododecanoic acid (13.9 g; 0.05 mole) in small portions over 10–15 minutes. The resulting white suspension is stirred for a further 30 minutes at 10° C. and is then allowed to warm to ambient temperature. Upon reaching ambient temperature, the reaction mixture is heated to reflux and maintained at this temperature for 3 hours. The reaction mixture is then cooled to 5° C. and treated with a solution of KOH (1.4 g; 0.025 mole) in ethanol (50 ml) followed by dodecyl bromide (6.2 g; 0.025 mole). The reaction mixture is allowed to warm to ambient temperature and is then heated to reflux and maintained at this temperature for 2 hours. The reaction mixture is cooled to ambient temperature and the solvent removed under reduced pressure. The residue is suspended in water (100 ml and acidified with concentrated HCl to pH 3. The acidified aqueous suspension is then extracted with either (200 ml) and the ether extract is washed with water (3×50 ml). The extract is dried over $MgSO_4$, filtered, then evaporated to yield 14.7 g (79 %) of a yellow viscous oil.

Analysis Found: C 63.22 %; H 9.80 %; N 5.32 %.

$C_{39}H_{71}N_3O_4S_3$ requires: C 63.11 %; H 9.64 %; N 5.66 %.

Examples 4 to 9

The rust inhibiting, antiwear, extreme pressure and anti-oxidant properties of the compounds of the invention are determined by the following methods:

TABLE 1

| Rust inhibition - ASTM D-665 (IP 135) Test |
|---|
| The method involves stirring a mixture of 300 ml of the oil under test with 30 ml of synthetic sea water, at a temperature of 60° C. (140° F.) with a cylindrical steel specimen completely immersed therein. It is customary to run the test for 24 h. This method of test is intended to indicate the ability of stream-turbine oils and heavier-than-water fluids, including those used for stream-turbine gears, to aid in preventing the rusting |

TABLE 1-continued

Rust inhibition - ASTM D-665 (IP 135) Test of ferreous parts should water become mixed with the oil. Measured is the degree of corrosion of the steel specimen.

| Example | Test Oil | Test result |
|---|---|---|
| — | Base Oil[1] (Control) | severe rust after 24 hrs |
| 4 | Base Oil containing 0.05% by weight product of Example 1 | no rust after 24 hrs |
| 5 | Base Oil containing 0.05% by weight product of Example 2 | no rust after 24 hrs |
| 6 | Base Oil containing 0.05% by weight product of Example 3 | no rust after 24 hrs |

TABLE 2

Extreme Pressure and Antiwear Properties ASTM D 2783-81 (IP 239/79) Test

The method using the Shell four-ball apparatus is employed to test for suitability for anti-wear protection. The following are determined:
(a) the weld load WL, as the load (in kg) at which the 4 balls weld together in the course of 10 seconds, and (b) the average wear scar diameter WSD at a load of 40 kg for 1 hour (in mm).

| | | Test result | |
|---|---|---|---|
| Example | Test Oil | Wear Scar Diameter (mm) | Weld Load [kg] |
| — | Base Oil[1] | 1.00 | 125 |
| 7 | Base Oil containing 0.05% by weight product of Example 1 | 0.60 | 145 |
| 8 | Base Oil containing 0.05% by weight product of Example 3 | 0.54 | 140 |

TABLE 3

Antioxidant Properties (ASTM D 2272 (IP 229) Test)

The oil oxidation test, Rotary Bomb Oxidation Test, is carried out in the following way. An oil sample of 50 ml is oxidised in an oxygen atmosphere, in a glass vessel, together with 5 ml of distilled water and a polished, catalytically active Cu spiral washed with petroleum ether.
The glass vessel is in a stainless steel bomb with a manometer. The bomb rotates axially at 100 rpm, at an angle of 30° to the horizontal, in an oil bath at 150° C. The oxygen pressure is initially about 620 kPA (90 psi), before heating, increases to exactly 1400 kPA at 150° C. and remains constant until oxidation has started. The test has ended when there has been a pressure drop of 175 kPA (25,4 psi). The time is recorded in minutes. Long time values correspond to a high degree in stabilizer effectiveness.

| Example | Test Oil | Bomb life |
|---|---|---|
| — | Base Oil[1] | 25 minutes |
| 9 | Base Oil containing 0.25% by weight product of Example 1 | 68 minutes |

[1]Turbine grade mineral oil of viscosity 31.6 mm²/s at 40° C., 4.6 mm²/s at 100° C. and a sulphur content of 0.6%.

What is claimed is:

1. A lubricant composition comprising a lubricating oil and, as a multifunctional additive, at least one compound of formula (I)

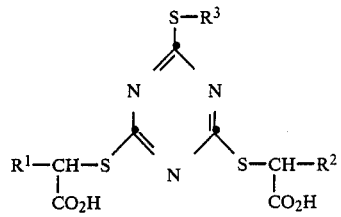

in which $R^1$ and $R^2$ are, independently, hydrogen or $C_1-C_{20}$ alkyl and $R_3$ is hydrogen, $C_1-C_{20}$ alkyl or a group of formula

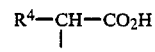

wherein $R^4$ is H or $C_1-C_{20}$ alkyl.

2. A lubricant composition according to claim 1, wherein the compounds of formula (I) are those in which $R^1$ and $R^2$ are $C_8-C_{20}$ alkyl and $R^3$ is $C_8-C_{20}$ alkyl or

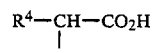

in which $R^4$ is $C_1-C_{20}$ alkyl.

3. A composition according to claim 1 wherein the amount of compound of formula (I) present ranges from 0.01-5 weight per cent based on the weight of the lubricant.

4. A composition according to claim 1, wherein the lubricating oil is a turbine oil or a hydraulic oil.

5. A compound having the formula (I):

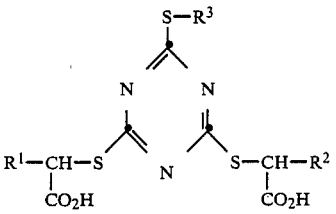

wherein $R^1$ and $R^2$ are, independently, hydrogen or $C_1-C_{20}$ alkyl and $R^3$ is hydrogen, $C_1-C_{20}$ alkyl or a group of the formula

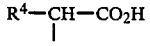

where $R^4$ is H or $C_1-C_{20}$ alkyl, with the proviso that when $R^3$ is $-CH_2CO_2H$ then $R^1$ and $R^2$ may not simultaneously be hydrogen.

6. A compound of formula I according to claim 5: 2,2', 2''-[1,3,5-triazine-2,4,6-triyltris(thio)]tris dodecanoic acid; 2,2', 2''-[1,3,5-triazine-2,4,6-triyltris-(thio)]tris octadecanoic acid or 2,2'-[2-dodecylthio-1,3,5-triazine-4,6-diylbis-(thio)]bis dodecanoic acid.

7. A lubricant composition according to claim 1 comprising, as a multifunctional additive, at least one compound of 2,2', 2''-[1,3,5-triazine-2,4,6-triyltris(thio)]tris dodecanoic acid; 2,2', 2''-[1,3,5-triazine-2,4,6-triyltris(thio)]tris octadecanoic acid or 2,2'-[2-dodecylthio-1,3,5-triazine-4,6-diylbis-(thio)]bis dodecanoic acid.

8. Process of improving the rust inhibiting, anti-wear, extreme pressure and antioxidant properties of lubricating oils by incorporation of at least one compound of formula I according to claim 1 into said lubricant.

* * * * *